(12) United States Patent
Usayapant et al.

(10) Patent No.: US 8,962,572 B2
(45) Date of Patent: Feb. 24, 2015

(54) BORTEZOMIB FORMULATIONS

(75) Inventors: Arunya Usayapant, Mundelein, IL (US); David Bowman, Mattawan, MI (US)

(73) Assignee: Fresenius Kabi USA, LLC, Lake Zurich, IL (US)

( * ) Notice: Subject to any disclaimer, the term of this patent is extended or adjusted under 35 U.S.C. 154(b) by 396 days.

(21) Appl. No.: 13/252,421

(22) Filed: Oct. 4, 2011

(65) Prior Publication Data

US 2012/0083457 A1 Apr. 5, 2012

Related U.S. Application Data

(60) Provisional application No. 61/390,046, filed on Oct. 5, 2010.

(51) Int. Cl.
| | | |
|---|---|---|
| *A61K 38/05* | (2006.01) | |
| *A61K 31/69* | (2006.01) | |
| *A61K 9/19* | (2006.01) | |
| *A61K 33/22* | (2006.01) | |
| *C07F 5/02* | (2006.01) | |
| *C07F 5/04* | (2006.01) | |
| *A61K 9/00* | (2006.01) | |

(52) U.S. Cl.
CPC .............. *A61K 31/69* (2013.01); *A61K 9/0019* (2013.01); *A61K 9/19* (2013.01); *A61K 33/22* (2013.01)
USPC ........................................... 514/21.91; 568/1

(58) Field of Classification Search
None
See application file for complete search history.

(56) References Cited

U.S. PATENT DOCUMENTS

| | | |
|---|---|---|
| 4,499,082 A | 2/1985 | Shenvi et al. |
| 5,106,948 A | 4/1992 | Kinder et al. |
| 5,169,841 A | 12/1992 | Kleeman et al. |
| 5,187,157 A | 2/1993 | Kettner et al. |
| 5,242,904 A | 9/1993 | Kettner et al. |
| 5,250,720 A | 10/1993 | Kettner et al. |
| 5,780,454 A | 7/1998 | Adams et al. |
| 6,066,730 A | 5/2000 | Adams et al. |
| 6,083,903 A | 7/2000 | Adams et al. |
| 6,297,217 B1 | 10/2001 | Adams et al. |
| 6,617,317 B1 | 9/2003 | Adams et al. |
| 6,699,835 B2 | 3/2004 | Plamondon et al. |
| 6,713,446 B2 | 3/2004 | Gupta |
| 6,747,150 B2 | 6/2004 | Adams et al. |
| 6,958,319 B2 | 10/2005 | Gupta |
| 7,109,323 B2 | 9/2006 | Plamondon et al. |
| 7,119,080 B2 | 10/2006 | Adams et al. |
| 8,263,578 B2 | 9/2012 | Soppimath et al. |
| 2009/0325903 A1 | 12/2009 | Elliott et al. |
| 2010/0247669 A1 | 9/2010 | Eliasof et al. |
| 2011/0230441 A1 | 9/2011 | Soppimath et al. |
| 2012/0035133 A1 | 2/2012 | Bricout et al. |

FOREIGN PATENT DOCUMENTS

| | | |
|---|---|---|
| WO | 2008075376 | 6/2008 |
| WO | 2010039762 | 4/2010 |
| WO | 2010089768 | 8/2010 |

OTHER PUBLICATIONS

Adams, et al., Semin. Oncol., 28(6):613-619 (2001).*
International Searching Authority, "International Search Report and Written Opinion for PCT/US2011/054703", Dec. 23, 2011, Publisher: European Patent Office.
Hall, D.G., "Structure, Properties, and Preparation of Boronic Acid Derivatives. Overview of Their Reactions and Applications", "Boronic Acids", 2005, pp. 1-8, 85-86.
Hematology/Oncology Pharmacy Association, "Differentiating Novel Agents in the Management of Multiple Myeloma: Navigating the Role of the Oncology Pharmacist", 2010, pp. 1-17, Publisher: Hematology/Oncology Pharmacy Association.
Liu, et al., "Dietary flavonoids inhibit the anticancer effects of the proteasome inhibitor bortezomib", "Blood", Jul. 16, 2008, pp. 3835-3846, vol. 112, No. 9.
Marinaro, et al., "Physical and Chemical Properties of Boronic Acids: Formulation Implications", 2006, pp. 1-2, Publisher: Department of Pharmaceutical Chemistry, The University of Kansas.
Marinaro, W.A., "Abstract of Ph.D. Thesis", 2008, p. 1, Publisher: University of Kansas.
Miguel, et al., "A Practical Update on the Use of Bortezomib in the Management of Multiple Myeloma", "The Oncologist", 2006, pp. 51-61, vol. 11.
Millennium Pharmaceuticals, Inc., "Highlights of Prescribing Information for Velcade", 2009, pp. 1-9, Publisher: Millennium Pharmaceuticals, Inc.
NIH Office of Technology Transfer, "VELCADE, New Science and New Hope: A Case Study", 2003, pp. 1-2, Publisher: NIH Office of Technology Transfer.
Pekol, et al., "Human Metabolism of the Proteasome Inhibitor Bortezomib: Identification of Circulating Metabolites", "Drug Metabolism and Disposition", 2005, pp. 771-777, vol. 33, No. 6.
Stella, et al., "Prodrug strategies to overcome poor water solubility", "Advanced Drug Delivery Reviews", 2007, pp. 677-694, vol. 59.

* cited by examiner

*Primary Examiner* — Maury Audet
(74) *Attorney, Agent, or Firm* — Blanchard & Associates

(57) ABSTRACT

A bortezomib composition includes bortezomib and boric acid in a mass ratio of boric acid to bortezomib is from 1:1 to 10:1. The composition is a solid, and may be prepared by forming a liquid mixture including a solvent, bortezomib and boric acid, and lyophilizing the liquid mixture.

20 Claims, 1 Drawing Sheet

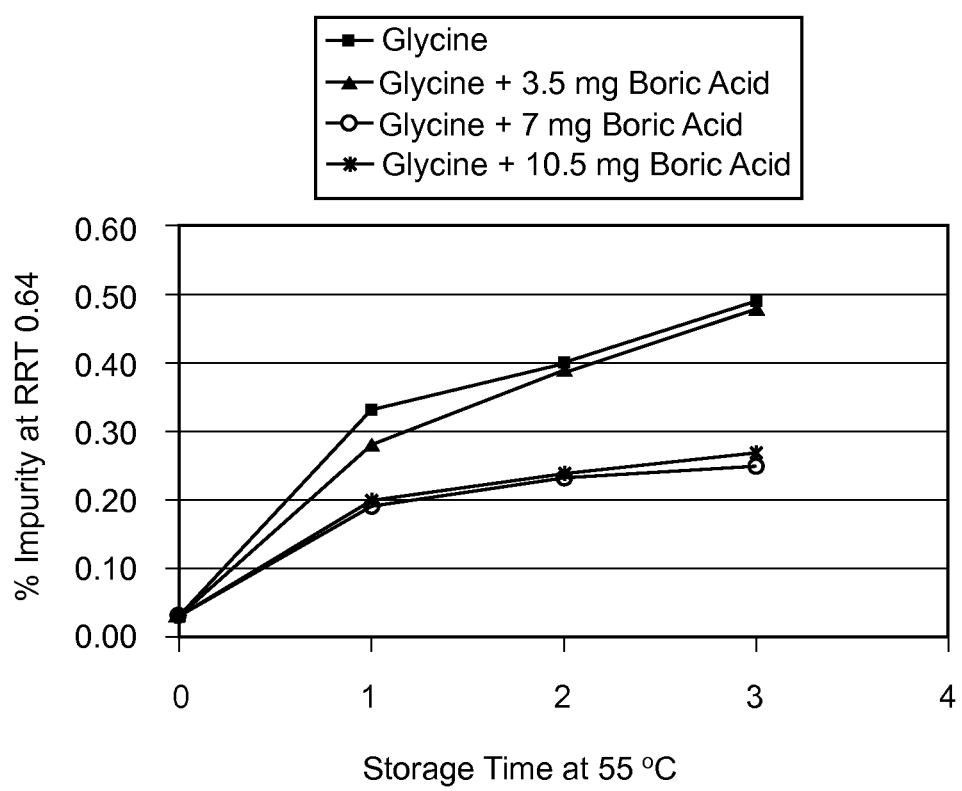

BORTEZOMIB FORMULATIONS

REFERENCE TO RELATED APPLICATIONS

This application claims the benefit of U.S. Provisional Application No. 61/390,046 entitled "Bortezomib Formulations" filed Oct. 5, 2010, which is incorporated by reference in its entirety.

BACKGROUND

Bortezomib is a modified di-peptidyl boronic acid that can inhibit proteosome in organisms. Bortezomib is believed to function as a reversible inhibitor of the chymotrypsin-like activity of the 26S proteasome in mammalian cells. The 26S proteasome is a large protein complex that degrades ubiquitinated proteins. The ubiquitin-proteasome pathway plays a role in regulating the intracellular concentration of specific proteins, maintaining homeostasis within cells. Inhibition of the 26S proteasome prevents this targeted proteolysis, which can affect multiple signaling cascades within the cell. This disruption of normal homeostatic mechanisms can lead to cell death.

Bortezomib is cytotoxic to a variety of cancer cell types in vitro and causes a delay in tumor growth in vivo in nonclinical tumor models, including multiple myeloma. Bortezomib presently is approved for the treatment of multiple myeloma, relapsed multiple myeloma, and mantle cell lymphoma. A variety of combination therapies have been investigated for treating multiple myeloma, in which bortezomib is administered with one or more other biologically active substances, such as lenalidomide, dexamethasone, melphalan, predisone, thalidomide, cyclophosphamide, doxorubicin, vincristine, carmustine, pomalidomide, vorinostat, tanespimycin, and perifosine. Other potential uses of bortezomib also have been reported, including treatment of amyloidosis.

Bortezomib is one of a number of peptidyl boronic acids and peptidyl boronic esters that potentially have biological activity. Non-limiting examples of biological activities reported for peptidyl boronic acids and esters include inhibition of trypsin-like proteases, inhibition of renin, inhibition of the growth of certain cancer cells, and inhibition of proteolytic enzymes. These biological activities may be related to physiological symptoms. For example, proteosome inhibitors can treat infarcts such as occur during stroke or myocardial infarction, and can treat inflammatory and autoimmune diseases. Other possible biological activities of peptidyl boronic acids and esters include reducing the rate of muscle protein degradation, reducing the activity of NF-κB in a cell, reducing the rate of degradation of p53 protein in a cell, inhibiting cyclin degradation in a cell, inhibiting the growth of a cancer cell, inhibiting antigen presentation in a cell, inhibiting NF-κB dependent cell adhesion, and inhibiting HIV replication.

A disadvantage that bortezomib shares with other peptidyl boronic acids and esters is an instability to standard conditions of purification and storage. Boronic acids and esters tend to form anhydrides, including cyclic anhydrides referred to as "boroxines," during dehydration, which can make it difficult to purify the desired compound. Boronic acids and esters also tend to oxidize in air, which can severely limit their shelf life. Thus, bortezomib typically is difficult to purify, to characterize and/or to formulate into a stable therapeutic product.

One conventional method of increasing the stability of bortezomib involves combining the boronic acid with a sugar or other compound having two or more hydroxyl groups separated by at least two connecting atoms (i.e. C, N, S or O). See, for example, U.S. Pat. No. 6,699,835 to Plamondon et al. It is reported that bortezomib forms a boronate ester with such a di-hydroxyl compound, and that this ester is more stable to air and to dehydration than bortezomib alone. Preferred di-hydroxyl compounds for this stabilization method are disclosed as the reduced sugars sorbitol and mannitol. In a specific embodiment of this method, a mixture of bortezomib, the sugar and a solvent is subjected to lyophilization to remove the solvent, providing a powder containing the bortezomib, the sugar and/or an ester of the bortezomib and the sugar.

This sugar stabilization method has been implemented in the formulation that is commercially available at present and is sold under the VELCADE® trademark. VELCADE® for Injection (Millennium Pharmaceuticals, Inc.; Cambridge, Mass., USA) is currently available as a lyophilized powder containing bortezomib and mannitol. A single dose of VELCADE® includes 3.5 milligrams (mg) bortezomib and 35 mg mannitol. VELCADE® is reconstituted by combining the lyophilized powder with 3.5 milliliters (mL) of 0.9% sodium chloride saline, to provide an injectable solution having a bortezomib concentration of 1 mg/mL.

An alternative method of increasing the stability of bortezomib that has been reported involves combining the compound with a cyclodextrin, a solubilizer, t-butyl alcohol, or one or more of an amino acid, a vitamin, a carboxylic acid and sodium chloride. The "solubilizer" may be a polyoxyethylene-polyoxypropylene copolymer, a fatty alcohol, a fatty alcohol derivative, a fatty acid, or a fatty acid derivative. See PCT Application Publication WO 2010/039762. A lyophilized powder formed from 3.5 mg bortezomib dissolved in 5 mL t-butyl alcohol is reported as having impurity levels below 0.5% (relative to the bortezomib content) after storage for 1 week at 60° C. in a closed container, at 40° C. and 75% relative humidity, or at 25° C. and 60% relative humidity.

The conventional stabilization methods described above have met with mixed success. It would be desirable to have a composition containing bortezomib that is stable for an extended period of time and that can be administered in a conventional way. It also would be desirable for such a composition to retain the therapeutic effectiveness of conventional bortezomib formulations.

SUMMARY

In one aspect, the invention provides a composition that includes bortezomib and boric acid. The composition is a solid, and the mass ratio of boric acid to bortezomib is from 1:1 to 10:1.

In another aspect of the invention, there is a method of making a solid composition that includes forming a liquid mixture including a solvent, bortezomib and boric acid, and lyophilizing the liquid mixture.

In another aspect of the invention, there is a composition, formed by a method that includes forming a liquid mixture including a solvent, bortezomib and boric acid, and lyophilizing the liquid mixture to form a solid composition. The mass ratio of boric acid to bortezomib in the liquid mixture is from 1:1 to 10:1.

To provide a clear and more consistent understanding of the specification and of the claims that follow, the following definitions are provided.

The term "mass ratio" of two substances means the mass of one substance (M1) relative to the mass of the other substance (M2), where both masses have identical units, expressed as M1:M2.

The term "chemical transformation" means the conversion of a substance into a product, irrespective of reagents or mechanisms involved.

The term "solution" means a homogeneous liquid phase containing two or more substances, where the two substances are intimately combined so as to behave physically as a single phase.

The term "emulsion" means a liquid phase containing two or more substances, where at least one substance is present as liquid droplets within at least one other substance.

The term "lyophilizing" means removing from a solution or an emulsion one or more substances having the lowest boiling points by freezing the solution or emulsion and applying a vacuum to the frozen mixture.

Other than in the operating examples, or where otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the following specification and claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, numerical values set forth in the specific examples are reported as accurately as possible. Any numerical value, however, inherently may contain certain errors resulting from the standard deviation found in their respective testing measurements.

The scope of the present invention is defined solely by the appended claims and is not affected by the statements within this summary.

BRIEF DESCRIPTION OF THE DRAWINGS

The invention can be better understood with reference to the following drawings and description. The components in the figures and in the chemical structures below are not necessarily to scale and are not intended to accurately represent molecules or their interactions, emphasis instead being placed upon illustrating the principles of the invention.

FIG. 1 is a graph of the amount of an impurity measured by High Pressure Liquid Chromatography (HPLC) (relative retention time=0.64) over time at 55° C. for bortezomib compositions containing glycine alone or with 3.5-10.5 mg boric acid.

DETAILED DESCRIPTION

A lyophilized formulation that includes bortezomib and boric acid can stabilize the bortezomib, while also providing for rapid reconstitution prior to administration to a patient. Stabilization of lyophilized bortezomib can provide for storage of the therapeutic substance at ambient temperatures for extended periods of time without allowing for significant degradation of the bortezomib. Rapid reconstitution, such as in saline, can provide for conventional administration of the therapeutic substance. Thus, the lyophilized formulation of bortezomib and boric acid has an advantageous combination of stability during storage and ease of administration.

A composition may include bortezomib, boric acid and optionally one or more other substances, where the composition is a solid. The mass ratio of boric acid to bortezomib preferably is from 1:1 to 10:1. If present in the composition, the mass ratio of the one or more other substances to bortezomib preferably is from 1:1 to 20:1. The solid composition may be prepared by forming a liquid mixture that includes a solvent, bortezomib, boric acid, and optionally one or more other substances, and lyophilizing the liquid mixture. The resulting solid composition may be used in administering bortezomib to a patient by combining the composition with an aqueous carrier to form a solution or emulsion, which, for example, can be injected into a patient.

Bortezomib, in its monomeric boronic acid form, is [(1R)-3-methyl-1-[[(2S)-1-oxo-3-phenyl-2-[(pyrazinylcarbonyl)] propyl]amino]butyl]boronic acid, and may be represented by structure I:

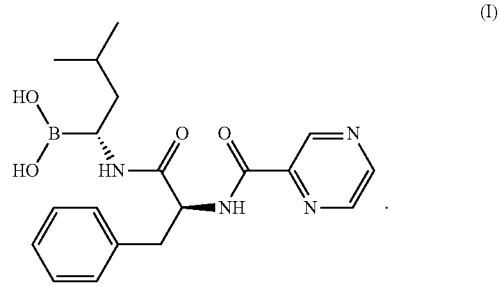 [SMILES: CC(C)C[C@H](NC(=O)[C@H](Cc1ccccc1)NC(=O)c1cnccn1)B(O)O ; "."]

(I)

In addition to its monomeric boronic acid structure, bortezomib may exist in one or more other structures, such as an anhydride structure. Bortezomib also may exist as a combination of its monomeric boronic acid structure with one or more of its other structures.

Bortezomib may form an anhydride when two or more molecules of the boronic acid compound of structure I condense into a single compound, with loss of one or more water molecules from the boronic acid moieties. When mixed with water, the boronic anhydride compound may hydrate to release two or more free boronic acid molecules represented by structure I. A boronic anhydride can include two, three, four, or more boronic acid moieties and can have a cyclic or linear configuration. Mixtures of the various anhydride structures of bortezomib can exist in combination with each other and/or with the monomeric boronic acid structure. Bortezomib in its cyclic dimer anhydride structure may be represented by structure II:

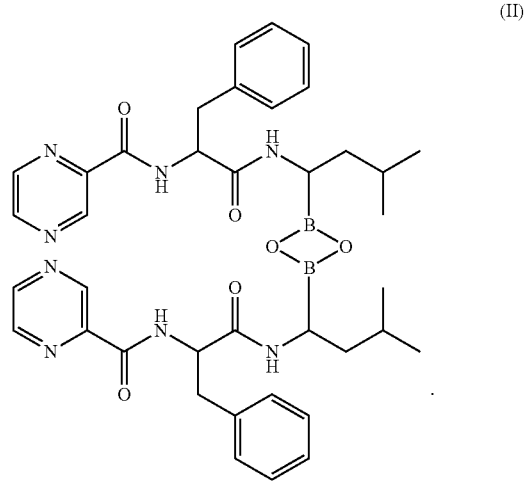 [SMILES: CC(C)CC(NC(=O)C(Cc1ccccc1)NC(=O)c1cnccn1)B1OB(C(CC(C)C)NC(=O)C(Cc2ccccc2)NC(=O)c2cnccn2)O1 ; "."]

(II)

Bortezomib in its cyclic trimer anhydride structure may be represented by structure III:

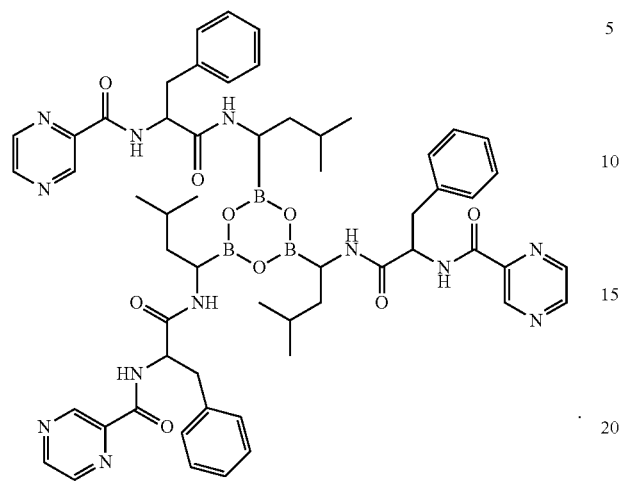

(III)

Bortezomib in an acyclic anhydride structure may be represented by structure IV, where x is an integer from 0 to 10:

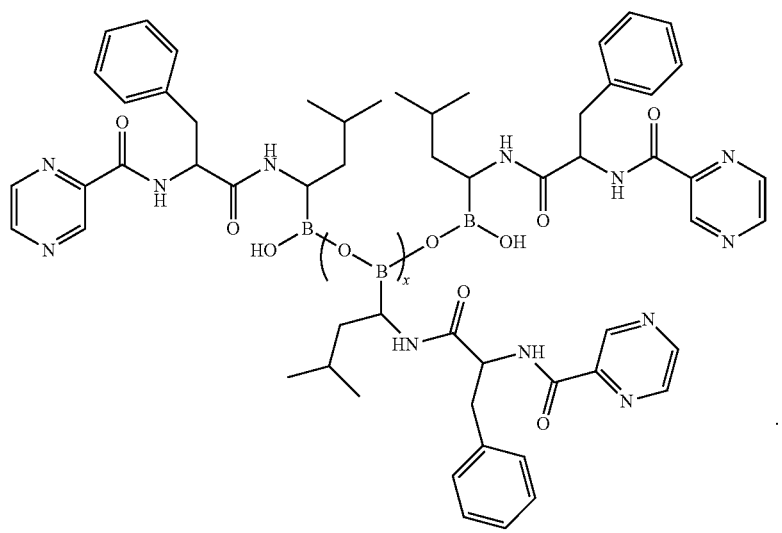

(IV)

Bortezomib also may form anhydride structures with other boronic acids and/or with boric acid, $B(OH)_3$. For example, a cyclic anhydride of bortezomib with boric acid may be represented by one or more of structures V, VI and VII:

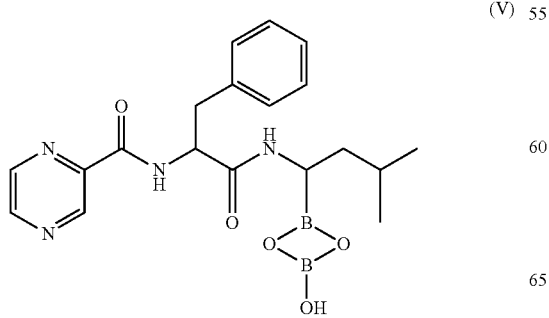

(V)

(VI)

(VII)

An acyclic anhydride of bortezomib with boric acid may be represented by structure VIII, where x is an integer from 0 to 10:

(VIII)

Bortezomib can degrade when exposed to air, likely due to oxidation reactions. Structure I can be described as a boric acid group, —B(OH)$_2$, bonded to a peptidyl group. Without being bound to any particular theory of operation whatsoever, oxidation of bortezomib as represented by structure I is believed to form free boric acid and one or more oxidized derivatives of the peptidyl group.

Previously, it was believed that stabilization of bortezomib from oxidative degradation required preventing the bortezomib from forming boronic anhydrides. It has been reported that boronic acids in the solid state autooxidize through a mechanism involving a boronic anhydride as an autooxidation initiator. See Hall, D. G., *Boronic Acids*, 2005, Wiley-VCH, p. 8. An increase in the amount of boronic anhydride present in a solid formulation of bortezomib would be expected to result in an increased susceptibility of the bortezomib to degradation. The presence of free boric acid in a solid composition containing bortezomib would be expected to increase the likelihood that boronic anhydrides may form. Thus, it would be expected that adding free boric acid to a solid composition containing bortezomib would decrease the stability of bortezomib in the composition.

Surprisingly, it has been discovered that boric acid can be present with bortezomib in the solid state without increasing the rate of degradation of the bortezomib. Even more surprisingly, boric acid can stabilize bortezomib in a solid composition at a level comparable to the stabilization observed in a conventional solid composition containing bortezomib and mannitol. This advantageous stabilization is observed in spite of the expectation that a solid composition including bortezomib and boric acid would include at least a portion of the bortezomib in one or more anhydride structures such as structures II-VIII.

Preferably when a solid composition including bortezomib and boric acid is stored at 55° C., at most 5% of the bortezomib degrades after 3 weeks. Degradation of bortezomib means a chemical transformation of bortezomib resulting in a substance other than an anhydride or a boronate ester. Preferably when a solid composition including bortezomib and boric acid is stored for 3 weeks at 55° C., at most 3% of the bortezomib degrades, more preferably at most 2% of the bortezomib degrades, more preferably at most 1% of the bortezomib degrades, and more preferably at most 0.5% of the bortezomib degrades.

The mass ratio of boric acid to bortezomib in a solid composition may be from 1:1 to 10:1. Preferably the mass ratio of boric acid to bortezomib in a solid composition may be from 1:1 to 4:1. More preferably the mass ratio of boric acid to bortezomib in a solid composition may be from 2:1 to 3:1, or about 3:1.

One possible consequence of protecting an otherwise unstable substance from degradation in the solid state by combining it with another substance is that the unstable substance may or may not be inhibited from subsequently dissolving in a solvent. For example, bortezomib can be stabilized in a solid composition with mannitol, while also rapidly dissolving in saline; however, when bortezomib is stabilized with a different polyol—dextran—it is resistant to dissolving in saline. As described in Example 3 below, a solid formulation of bortezomib and dextran can stabilize the bortezomib at a level comparable to that provided by a conventional solid formulation of bortezomib and mannitol. The dextran formulation, however, required 9 minutes to be reconstituted in saline, whereas the conventional mannitol formulation required only 1.25 minutes. See Example 4 and Table 4, below. Thus, one of ordinary skill in the art would not be able to predict whether a solid composition that protects bortezomib against degradation would also allow for rapid reconstitution of the bortezomib in a solvent.

It has been discovered that bortezomib present with boric acid in a solid composition can have surprisingly rapid reconstitution times in an aqueous liquid such as saline. More surprisingly, the presence of boric acid in a solid composition containing bortezomib and mannitol can reduce the reconstitution time relative to that of the conventional composition containing only bortezomib and mannitol. See Example 5 and Table 5, below. Thus, solid compositions containing bortezomib and boric acid can provide an unpredictably advantageous combination of high stability and rapid reconstitution time.

Preferably when a solid composition including bortezomib and boric acid is combined with a 0.9% sodium chloride saline solution at a concentration of 1 milligram (mg) bortezomib per milliliter (mL) saline and manually shaken every 15 seconds at room temperature, a solution or emulsion is formed within 4 minutes. More preferably when a solid composition including bortezomib and boric acid is combined with a 0.9% NaCl saline solution at a bortezomib concentration of 1 mg/mL saline and manually shaken every 15 seconds at room temperature, a solution or emulsion is formed within 3.5 minutes. More preferably a solution or emulsion is formed within 3 minutes, more preferably within 2.5 minutes, more preferably within 2 minutes, more preferably within 1.5 minutes, more preferably within 1 minute, and more preferably within 30 seconds. A reconstitution time of 2 minutes or less is desirable for injectable formulations used for non-emergency administration.

A solid composition including bortezomib and boric acid may include one or more other substances. Non-limiting examples of other substances include bulking agents, carriers, diluents, fillers, salts, buffers, stabilizers, solubilizers, preservatives, antioxidants, and tonicity contributors. Substances that may be useful in formulating pharmaceutically acceptable compositions, and methods of forming such compositions, are described for example in Remington: The Science and Practice of Pharmacy, 20th Ed., ed. A. Gennaro, Lippincott Williams & Wilkins, 2000, and in Kibbe, "Handbook of Pharmaceutical Excipients,"$3^{rd}$ Edition, 2000.

In one example, a solid composition including bortezomib and boric acid includes a bulking agent. Non-limiting examples of bulking agents include amino acids and saccharides. Non-limiting examples of amino acids include glycine. Non-limiting examples of saccharides include dextran, mannitol, lactose, sucrose, trehalose, dextrose, starch, hydroxyethylstarch, cellulose, polysaccharides, and cyclodextrins. If the saccharide includes two or more alcohol (—OH) functional groups, at least a portion of the bortezomib may be present as a boronate ester of the saccharide. Boronate esters formed from bortezomib and compounds having two or more alcohol groups are described, for example in U.S. Pat. No. 6,699,835 to Plamondon et al.

A solid composition including bortezomib and boric acid may include an amino acid such as glycine. A solid composition including bortezomib, boric acid and glycine may have a mass ratio of glycine to bortezomib of from 1:1 to 20:1. Preferably a solid composition including bortezomib, boric acid and glycine may have a mass ratio of glycine to bortezomib of from 5:1 to 15:1. More preferably a solid composition including bortezomib, boric acid and glycine may have a mass ratio of glycine to bortezomib of from 7:1 to 10:1, or about 7:1.

A solid composition including bortezomib and boric acid may include a saccharide such as dextran. A solid composition including bortezomib, boric acid and dextran may have a mass ratio of dextran to bortezomib of from 1:1 to 20:1. Preferably a solid composition including bortezomib, boric acid and dextran may have a mass ratio of dextran to bortezomib of from 5:1 to 15:1. More preferably a solid composition including bortezomib, boric acid and dextran may have a mass ratio of dextran to bortezomib of from 7:1 to 10:1.

A solid composition including bortezomib and boric acid may include a saccharide such as a cyclodextrin, for example hydroxypropyl-β-cyclodextrin. A solid composition including bortezomib, boric acid and a cyclodextrin may have a mass ratio of cyclodextrin to bortezomib of from 1:1 to 20:1. Preferably a solid composition including bortezomib, boric acid and a cyclodextrin may have a mass ratio of cyclodextrin to bortezomib of from 5:1 to 15:1. More preferably a solid composition including bortezomib, boric acid and a cyclodextrin may have a mass ratio of cyclodextrin to bortezomib of from 7:1 to 10:1.

A solid composition including bortezomib and boric acid may include a saccharide having two or more alcohol functional groups such as mannitol. A solid composition including bortezomib, boric acid and mannitol may have a mass ratio of mannitol to bortezomib of from 1:1 to 20:1. Preferably a solid composition including bortezomib, boric acid and mannitol may have a mass ratio of mannitol to bortezomib of from 5:1 to 15:1. More preferably a solid composition including bortezomib, boric acid and mannitol may have a mass ratio of mannitol to bortezomib of from 7:1 to 10:1.

A solid composition including bortezomib, boric acid and optionally one or more other substances may be prepared by forming a liquid mixture that includes a solvent, bortezomib, boric acid, and optionally one or more other substances, and lyophilizing the liquid mixture. The liquid mixture may be formed by adding the bortezomib, boric acid, and optionally one or more other substances to a container including the solvent. The lyophilizing may include freeze-drying the liquid mixture to provide a solid composition.

The solvent in the liquid mixture may include water and/or an organic solvent. Preferably the solvent includes both water and an organic solvent, where the organic solvent is miscible with water. The concentration of organic solvent in the solvent may be from 1 to 20 percent by volume (vol %), and preferably may be from 2 to 10 vol %. Non-limiting examples of organic solvents that are miscible with water and may be present in the solvent include alcohols such as ethanol, isopropanol, and t-butanol. Preferably the solvent in the liquid mixture includes water and ethanol.

The liquid mixture may include a solvent containing water and from 1 to 20 vol % organic solvent, bortezomib at a concentration of from 0.5 to 5 mg/mL, boric acid at a concentration of from 0.5 mg/mL to 20 mg/mL, and optionally another substance at a concentration of from 5 to 50 mg/mL. Preferably the liquid mixture may include a solvent containing water and from 2 to 10 vol % alcohol, bortezomib at a concentration of from 1 to 4 mg/mL, boric acid at a concentration of from 1 mg/mL to 16 mg/mL, and optionally at least one other substance at a concentration of from 10 to 40 mg/mL. More preferably the liquid mixture may include a solvent containing water and from 2 to 10 vol % ethanol, bortezomib at a concentration of from 1.5 to 3 mg/mL, boric acid at a concentration of from 1.5 mg/mL to 12 mg/mL, and optionally at least one other substance at a concentration of from 15 to 30 mg/mL.

In one example, the liquid mixture may be prepared by combining bortezomib and boric acid in water. In another example, the liquid mixture may be prepared by forming an aqueous liquid containing water, bortezomib and boric acid, forming an organic liquid containing an organic solvent and the at least one other substance, and combining the aqueous liquid and the organic liquid. In another example, the liquid mixture may be prepared by forming a solvent including water and an organic solvent, and adding to the solvent the bortezomib, boric acid and optionally at least one other substance.

The liquid mixture may then be lyophilized to form a solid composition, such as by subjecting the liquid mixture to freeze-drying. Freeze-drying of the liquid mixture may include maintaining the liquid mixture in an inert atmosphere, such as nitrogen or argon.

In one example, 2 mL of a liquid mixture is added to a 10 mL vial, the vial is then placed in a freeze-dryer, and the liquid mixture is then lyophilized to form a solid composition. The liquid mixture may contain water, from 2 to 10 vol % ethanol, from 3 to 4 mg bortezomib, from 3.5 to 35 mg boric acid, and up to 35 mg glycine. Preferably the liquid mixture contains water, about 5 vol % ethanol, about 3.5 mg bortezomib, about 10.5 mg boric acid, and about 25 mg glycine.

A solid composition including bortezomib, boric acid and optionally one or more other substances may be administered to a patient by combining the composition with an aqueous carrier liquid to form an aqueous solution or emulsion, and administering the aqueous solution or emulsion into the patient by, for example, injection. Preferably, the aqueous carrier liquid is a pharmaceutically acceptable carrier liquid. Non-limiting examples of pharmaceutically acceptable carrier liquids include water and saline, such as phosphate buffered saline (PBS) and Ringer's solution. The aqueous carrier liquid also may include fixed oils, fatty esters or polyols, particularly if the aqueous mixture for injection is a suspension. The aqueous carrier liquid also may include one or more other substances such as buffers, stabilizers, solubilizers, preservatives and antioxidants.

Boric acid may be combined with other peptidyl boronic acids and esters, and these combinations also may have desirable combinations of stability and reconstitution times. Non-limiting examples of other peptidyl boronic acids and esters are described, for example in U.S. Pat. No. 6,617,317 to Adams et al.

The following examples are provided to illustrate one or more preferred embodiments of the invention in a non-limiting manner. Numerous variations can be made to the following examples that lie within the scope of the invention.

EXAMPLES

Example 1

Formation of Bortezomib Compositions

Bortezomib (350 mg) was combined with 10 mL ethanol, and the mixture was stirred to form a bortezomib stock solution. In a separate container, 700 mg boric acid was combined with 20 mL purified water, and the mixture was stirred to form a boric acid stock solution. In a 50-mL volumetric flask, approximately 875 mg glycine was combined with 30 mL purified water, and to this mixture was added 7.5 mL of the boric acid stock solution, 2.5 mL of the bortezomib stock solution, and additional purified water to provide a lyophilization mixture having a total volume of 50 mL.

In this example, the lyophilization mixture was a liquid mixture containing a solvent, bortezomib and boric acid, where the solvent included water and about 5 vol % organic solvent (ethanol; 100%×[~2.5 mL ethanol from bortezomib stock solution/50 mL total volume]=100%×2.5 mL/50 mL=100%×0.05=5 vol %), where the mass ratio of boric acid to bortezomib was about 3:1 ([700 mg boric acid in stock solution×0.375 of stock solution]:[350 mg bortezomib in stock solution×0.25 of stock solution]=262.5 mg boric acid: 87.5 mg bortezomib=3:1), and where the mass ratio of glycine to bortezomib was about 10:1 (875 mg glycine:[350 mg bortezomib in stock solution×0.25 of stock solution]=875 mg glycine:87.5 mg bortezomib=10:1).

Approximately 2 mL aliquots of the lyophilization mixture were placed in separate 10 mL glass vials, and then the liquid mixtures were lyophilized as follows. Split rubber stoppers were partially inserted into the vials, and the vials were placed in a freeze-dryer with a shelf temperature of −40° C. The temperature was maintained at −40° C. for 3 hours, allowed to increase to −10° C. and maintained at −10° C. for 3 hours, and then lowered to −40° C. and maintained at −40° C. for 3 hours. Primary drying was performed at −15° C. under vacuum (200 mTorr) for 18 hours, and then secondary drying was performed at 25° C. under vacuum (200 mTorr) for 4 hours to form a solid composition. At the end of the lyophilization, the vials containing the resulting solid compositions were completely closed with the stoppers and removed from the freeze-dryer.

In this example, the solid composition included bortezomib, boric acid and glycine, with at most trace amounts of water and/or ethanol. The mass ratio of boric acid to bortezomib was about 3:1 ([700 mg boric acid in stock solution× 0.375 of stock solution]:[350 mg bortezomib in stock solution×0.25 of stock solution]=262.5 mg boric acid:87.5 mg bortezomib=3:1). The mass ratio of glycine to bortezomib was about 10:1 (875 mg glycine:[350 mg bortezomib in stock solution×0.25 of stock solution]=875 mg glycine:87.5 mg bortezomib=10:1).

Example 2

Large-Scale Formation of Bortezomib Compositions

Cool water for injection (9 Liters, USP, 15°-30° C.) was added to a clean compounding vessel covered with aluminum foil to protect the interior from light and then sparged with nitrogen until the dissolved oxygen level was below 2 parts per million (ppm). Boric acid (51 grams) was added to the water and mixed at room temperature (15°-30° C.) until dissolved. Glycine (150 grams) was then added, and the liquid was mixed at room temperature until the glycine was dissolved. Approximately 1,500 mL of this solution was removed and reserved for use as a rinse solution.

Dehydrated ethanol (600 mL) was added to another glass container protected from light, and boric acid (12 g) was added and mixed at room temperature until dissolved. Bortezomib (21 g) was then added and mixed until dissolved to form a bortezomib stock solution. The bortezomib stock solution was added to the compounding vessel, the glass container used for the bortezomib stock solution was rinsed with approximately 500 mL of the rinse solution, and the rinsate was transferred to the compounding vessel. The rinsing was repeated three times, using all of the rinse solution.

Sparged water for injection was added to the compounding vessel to obtain a final volume of 12 liters, and the liquid was mixed for approximately 10 minutes. The mixture was pre-filtered through a 0.45 micron filter and subsequently through a 0.22 micron filter. Aliquots (2 mL) of the filtered solution were added to vials that were then partially stoppered. In this example, the filtered solution was a liquid mixture containing a solvent, bortezomib and boric acid, where the solvent included water and about 5 vol % organic solvent (ethanol; 100%×[600 mL ethanol in bortezomib stock solution/12 L total volume]=100%×0.6 L/12 L=5 vol %), where the mass ratio of boric acid to bortezomib was about 3:1 (63 g boric acid in both solutions:21 g bortezomib in stock solution), and where the mass ratio of glycine to bortezomib was about 7:1 (150 g glycine:21 g bortezomib=7.14:1).

The liquid mixtures were lyophilized as follows. The partially stoppered vials were placed on lyophilizer chamber shelves at 5° C., and cooled at a rate of 1° C. per minute (° C./min) to a temperature of −40° C. After three hours, the freeze dryer chamber was evacuated, and the chamber pressure was adjusted to 200 microns with sterile nitrogen. The lyophilizer chamber shelves were warmed to −15° C. using a ramp rate of 0.1° C./min, and held at that temperature for 20-30 hours. After thermocouples in certain of the samples in the vials provided a temperature reading of −15±3° C., the shelf temperature was adjusted to 25° C. over approximately three hours using a ramp rate of 0.2° C./min and maintained at that temperature for 10 hours to form a solid composition. At the end of the terminal drying phase, the chamber pressure was restored using sterile nitrogen, and the vials containing the resulting solid compositions were sealed and removed. In this example, the solid composition included bortezomib, boric acid and glycine, with at most trace amounts of water and/or ethanol, where the mass ratio of boric acid to bortezomib was about 3:1, and the mass ratio of glycine to bortezomib was about 7:1 (see above paragraph for calculations).

Example 3

Accelerated Stability Screening of Bortezomib Compositions

Solid compositions containing 3.5 mg bortezomib were prepared using the general procedure of Example 1, but changing the amounts of the boric acid. In addition, solid compositions containing 3.5 mg bortezomib were prepared using the general procedure of Example 1, but changing the amounts of the boric acid and replacing the glycine with dextran (with or without boric acid) or mannitol (without boric acid). Relative amounts of each ingredient in the solid compositions are listed in Tables 1-3, below.

The solid lyophilized compositions were stored at 55° C. for 3 weeks. Samples were removed from each composition at the start of the storage and at the end of weeks 1, 2 and 3, and these samples were analyzed by HPLC for the impurities having peaks at RRT=0.64 (A), 1.07 (B), and 1.16 (C). The amount of each impurity was calculated as a percentage of the amount of bortezomib originally present in the sample, and the results are listed in Tables 1-3. The total percentage of impurities A, B and C for each sample was taken as the approximate percentage of degraded bortezomib in the sample.

TABLE 1

Accelerated Stability of Bortezomib Compositions at 55° C. (Impurity A)

| Ingredients, in addition to 3.5 mg Bortezomib (mg) | | | | Impurity at RRT = 0.64 by HPLC (%) | | | |
|---|---|---|---|---|---|---|---|
| Mannitol | Glycine | Dextran | Boric Acid | Start | 1 week | 2 weeks | 3 weeks |
| 35 | — | — | — | 0.02 | 0.14 | 0.20 | 0.23 |
| — | 35 | — | — | 0.03 | 0.33 | 0.40 | 0.49 |
| — | 35 | — | 3.5 | 0.03 | 0.28 | 0.39 | 0.48 |
| — | 35 | — | 7.0 | 0.03 | 0.19 | 0.23 | 0.25 |
| — | 35 | — | 10.5 | 0.03 | 0.20 | 0.24 | 0.27 |
| — | — | 35 | — | 0.02 | 0.13 | 0.19 | 0.22 |
| — | — | 35 | 3.5 | 0.03 | 0.28 | 0.29 | 0.24 |
| — | — | 35 | 10.5 | 0.02 | 0.20 | 0.22 | 0.24 |

TABLE 2

Accelerated Stability of Bortezomib Compositions at 55° C. (Impurity B)

| Ingredients, in addition to 3.5 mg Bortezomib (mg) | | | | Impurity at RRT = 1.07 by HPLC (%) | | | |
|---|---|---|---|---|---|---|---|
| Mannitol | Glycine | Dextran | Boric Acid | Start | 1 week | 2 weeks | 3 weeks |
| 35 | — | — | — | 0.40 | 0.29 | 0.26 | 0.26 |
| — | 35 | — | — | 0.72 | 0.61 | 0.58 | 0.58 |
| — | 35 | — | 3.5 | 0.68 | 0.48 | 0.53 | 0.57 |
| — | 35 | — | 7.0 | 0.52 | 0.37 | 0.46 | 0.46 |
| — | 35 | — | 10.5 | 0.56 | 0.44 | 0.47 | 0.47 |
| — | — | 35 | — | 0.51 | 0.36 | 0.33 | 0.33 |
| — | — | 35 | 3.5 | 0.51 | 0.34 | 0.31 | 0.31 |
| — | — | 35 | 10.5 | 0.45 | 0.32 | 0.33 | 0.35 |

TABLE 3

Accelerated Stability of Bortezomib Compositions at 55° C. (Impurity C)

| Ingredients, in addition to 3.5 mg Bortezomib (mg) | | | | Impurity at RRT = 1.16 by HPLC (%) | | | |
|---|---|---|---|---|---|---|---|
| Mannitol | Glycine | Dextran | Boric Acid | Start | 1 week | 2 weeks | 3 weeks |
| 35 | — | — | — | 0.05 | 0.04 | 0.03 | 0.02 |
| — | 35 | — | — | 0.16 | 0.18 | 0.17 | 0.16 |
| — | 35 | — | 3.5 | 0.16 | 0.12 | 0.14 | 0.16 |
| — | 35 | — | 7.0 | 0.10 | 0.06 | 0.10 | 0.09 |
| — | 35 | — | 10.5 | 0.12 | 0.09 | 0.10 | 0.09 |
| — | — | 35 | — | 0.07 | 0.05 | 0.05 | 0.04 |
| — | — | 35 | 3.5 | 0.09 | 0.05 | 0.04 | 0.04 |
| — | — | 35 | 10.5 | 0.07 | 0.04 | 0.04 | 0.04 |

The bortezomib compositions containing glycine and either 7 mg or 10.5 mg boric acid had a smaller amount of each impurity at each time sampled, relative to bortezomib and glycine alone, and relative to bortezomib combined with glycine and 3.5 mg boric acid.

The total percentage of impurities (A+B+C) for the bortezomib composition containing glycine and 3.5 mg boric acid was 1.21% after 3 weeks at 55° C. (0.48% A+0.57% B+0.16% C). Thus, at most 2% of the bortezomib degraded when this composition was stored at 55° C. for 3 weeks. The total percentage of impurities (A+B+C) after 3 weeks at 55° C. for the bortezomib compositions containing glycine and 7 mg or 10.5 mg boric acid was 0.8% and 0.83%, respectively (0.8%=0.25% A+0.46% B+0.09% C; and 0.83%=0.27% A+0.47% B+0.09% C). Thus, at most 1% of the bortezomib degraded when these compositions were stored at 55° C. for 3 weeks. In comparison, the total percentage of impurities (A+B+C) after 3 weeks at 55° C. for the conventional composition containing bortezomib and mannitol was 0.51% (0.23% A+0.26% B+0.02% C).

The amount of Impurity A (RTT=0.64) for the bortezomib compositions containing glycine and either 7 mg or 10.5 mg boric acid was comparable to that of the conventional bortezomib composition containing mannitol. FIG. 1 is a graph of the amounts of Impurity A measured over time for the bortezomib compositions containing glycine alone or with 3.5-10 mg boric acid.

Example 4

Reconstitution Time of Bortezomib Compositions

Solid compositions containing 3.5 mg bortezomib were prepared using the general procedure of Example 1, but changing the amounts of the boric acid and of the glycine. In addition, solid compositions containing 3.5 mg bortezomib were prepared using the general procedure of Example 1, but changing the amounts of the boric acid, and replacing the glycine with dextran or hydroxypropyl-β-cyclodextrin (with or without boric acid) or with mannitol (without boric acid). Relative amounts of each ingredient in the solid compositions are listed in Table 4.

A sample of each solid lyophilized composition was reconstituted by combining it with 3.5 mL of 0.9% sodium chloride saline (USP) at room temperature, and manually shaking each mixture every 15 seconds until a solution was formed. The resulting solutions corresponded to the conventional dosage and concentration of an injectable solution of bortezomib for administration. The times required for complete dissolution of each lyophilized composition in the saline are listed in Table 4.

TABLE 4

Reconstitution Times of Bortezomib Compositions
Ingredients, in addition to 3.5 mg Bortezomib (mg)

| Mannitol | Glycine | Dextran | Hydroxypropyl-β-cyclodextrin | Boric Acid | Reconstitution Time (min) |
|---|---|---|---|---|---|
| 35 | — | — | — | — | 1.25 |
| — | 35 | — | — | — | 9 |
| — | 35 | — | — | 3.5 | 3.5 |
| — | 35 | — | — | 7.0 | 2.5 |
| — | 35 | — | — | 10.5 | 2.5 |
| — | 25 | — | — | 7.0 | <1 |
| — | 25 | — | — | 10.5 | <1 |
| — | 25 | — | — | 14 | <1 |
| — | — | 35 | — | — | 9 |
| — | — | 35 | — | 3.5 | 3.5 |
| — | — | 35 | — | 10.5 | 4 |
| — | — | — | 25 | — | >10 |
| — | — | — | 25 | 10 | <1 |

The bortezomib compositions containing glycine and boric acid had substantially reduced reconstitution times relative to bortezomib compositions containing glycine alone. The reconstitution time of the composition containing boric acid and glycine was over 60% shorter than that of the composition containing glycine without boric acid (~61% reduction=100%×[9 min−3.5 min]/9 min). A reduction in reconstitution time when boric acid was present also was observed for bortezomib compositions containing dextran or hydroxypropyl-β-cyclodextrin. For the bortezomib compositions containing glycine, an increase in the boric acid content from 3.5 to 7 mg or 10.5 mg corresponded to a further decrease in the reconstitution time from 3.5 to 2.5 minutes, which was an overall reduction of over 70% (~72% reduction=100%×[9 min−2.5 min]/9 min).

The bortezomib compositions containing 25 mg glycine and from 7 to 14 mg boric acid had reconstitution times of less than one minute, which was at least 25% shorter than that of the conventional composition containing mannitol (~25% reduction=100%×[1.25 min−1 min]/1.25 min). The bortezomib composition containing 25 mg hydroxypropyl-β-cyclodextrin and 10 mg boric acid also had a reconstitution time of less than one minute.

Example 5

Analysis of Bortezomib Stability and Solubility in Solid Formulations

Solid compositions containing 3.5 mg bortezomib were prepared using the general procedure of Example 1, but changing the amounts of the boric acid. In addition, solid compositions containing 3.5 mg bortezomib were prepared using the general procedures of Example 1, but changing the amounts of boric acid and replacing the glycine with mannitol. Relative amounts of each ingredient in the solid compositions are listed in Table 5, below. Each solid composition was formed by lyophilizing a 2 mL aliquot containing the listed ingredients and 0.1 mL ethanol.

TABLE 5

Stability and Reconstitution of Bortezomib Compositions

| | Ingredients, in addition to 3.5 mg Bortezomib (mg) | | | Total Impurities by HPLC (%) | | | | Reconstitution |
|---|---|---|---|---|---|---|---|---|
| | Boric Acid | Glycine | Mannitol | Start | 1 week | 2 weeks | 3 weeks | Time (sec) |
| A | 10.5 | — | — | 0.4 | 0.4 | 0.5 | 0.4 | 60 |
| B | 35.0 | — | — | 0.4 | 0.5 | 0.6 | 0.4 | 30 |
| C | 10.5 | — | 25.0 | 0.3 | 0.4 | 0.4 | 0.3 | 15 |
| D | — | — | 25.0 | 0.4 | 0.5 | 0.4 | 0.3 | 45 |
| E | — | 25.0 | — | 0.4 | 0.5 | 0.5 | 0.5 | 300 |
| F | 10.5 | 25.0 | — | 0.4 | 0.5 | 0.4 | 0.5 | 30 |
| G | 17.5 | 25.0 | — | 0.5 | 0.6 | 0.5 | 0.5 | 90 |
| H | 35.0 | 25.0 | — | 0.5 | 0.6 | 0.5 | 0.5 | 120 |

For stability testing, portions of the lyophilized compositions were stored at 55° C. for 3 weeks. Samples were removed from each portion at the start of the storage and at the end of weeks 1, 2 and 3, and these samples were analyzed by HPLC for all impurities. The total amount of the impurities was calculated as a percentage of the amount of bortezomib originally present in the sample, and the results are listed in Table 5. The total percentage of impurities for each sample was taken as the approximate percentage of degraded bortezomib in the sample.

The stability of bortezomib in these lyophilized compositions was substantially unaffected by changes in the excipients. No stability trends were observed regarding the absence, presence or amount of boric acid, or regarding the absence, presence or amount of glycine or mannitol. All of the compositions maintained an impurity level of 0.4-0.6% for 3 weeks at 55° C.

For solubility testing, a sample of each solid lyophilized composition was reconstituted by combining it with 3.5 mL of 0.9% sodium chloride saline (USP) at room temperature, and manually shaking each mixture every 15 seconds until a solution was formed. The resulting solutions corresponded to the conventional dosage and concentration of an injectable solution of bortezomib for administration. The times required for complete dissolution of each lyophilized composition in the saline are listed in Table 5.

The bortezomib compositions containing boric acid had substantially shorter reconstitution times relative to comparable bortezomib compositions that did not contain boric acid. For the compositions containing glycine, the lyophilized powder without boric acid was difficult to wet during reconstitution, and the resulting liquid was not clear. The presence of boric acid in a mass ratio of 3:1 with bortezomib, however, provided a reconstitution time of 30 seconds for the composition containing glycine, resulting in a clear solution. The 30 second reconstitution time for the composition containing boric acid corresponded to at least a 90% reduction in reconstitution time relative to that of the composition containing glycine without boric acid (90% reduction=100%× [300 sec−30 sec]/300 sec). Increases in the amount of boric acid to mass ratios of 5:1 or 10:1 provided reconstitution times of 90 seconds and of 2 minutes, respectively. These reconstitution times corresponded to reductions of at least 70% and 60%, respectively, relative to that of the composition containing glycine without boric acid (70% reduction=100%×[300 sec−90 sec]/300 sec; and 60% reduction=100%×[300 sec−120 sec]/300 sec).

For the compositions containing mannitol, the presence of boric acid provided more than a 65% decrease in the reconstitution time, from 45 seconds to 15 seconds (~67% reduction=100%×[45 sec−15 sec]/45 sec). Thus, the composition containing both boric acid and mannitol dissolved more rapidly than the conventional composition containing only mannitol.

In the absence of the excipients glycine and mannitol, the bortezomib composition having a higher mass ratio of boric acid to bortezomib dissolved more rapidly. The composition having a 3:1 mass ratio of boric acid and the composition having a 10:1 mass ratio each provided a clear solution within 1 minute. Thus, an excipient such as glycine or mannitol was not necessary to provide an acceptable reconstitution time for a solid composition containing bortezomib and boric acid.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A composition, comprising:
bortezomib, and
boric acid;
where the composition is a solid, and
the mass ratio of boric acid to bortezomib is from 1:1 to 10:1.

2. The composition of claim 1, where the mass ratio of boric acid to bortezomib is from 1:1 to 4:1.

3. The composition of claim 1, where the mass ratio of boric acid to bortezomib is from 2:1 to 3:1.

4. The composition of claim 1, further comprising at least one other substance selected from the group consisting of an amino acid and a saccharide.

5. The composition of claim 1, further comprising glycine, where the mass ratio of glycine to bortezomib is from 1:1 to 20:1.

6. The composition of claim 5, where the mass ratio of glycine to bortezomib is from 5:1 to 15:1.

7. The composition of claim 5, where the mass ratio of glycine to bortezomib is from 7:1 to 10:1.

8. The composition of claim 5, where the mass ratio of boric acid to bortezomib is about 3:1, and the mass ratio of glycine to bortezomib is about 7:1.

9. The composition of claim 8, comprising about 3.5 mg bortezomib, about 10.5 mg boric acid, and about 25 mg glycine.

10. The composition of claim 1, further comprising mannitol, where the mass ratio of mannitol to bortezomib is from 1:1 to 20:1.

11. The composition of claim 1, where at least a portion of the bortezomib is present in an anhydride structure.

12. The composition of claim 1, where at least a portion of the bortezomib and boric acid are present together in an anhydride structure.

13. The composition of claim 1, where when the composition is stored at 55° C., at most 5% of the bortezomib degrades after 3 weeks.

14. The composition of claim 1, where when the composition is stored at 55° C., at most 2% of the bortezomib degrades after 3 weeks.

15. The composition of claim 1, where when the composition is stored at 55° C., at most 1% of the bortezomib degrades after 3 weeks.

16. The composition of claim 1, where when the composition is stored at 55° C., at most 0.5% of the bortezomib degrades after 3 weeks.

17. The composition of claim 1, where
when the composition is combined with a 0.9% NaCl saline solution at a bortezomib concentration of 1 mg/mL saline and manually shaken every 15 seconds,
the composition forms a solution or an emulsion within 4 minutes.

18. The composition of claim 17, where the composition forms the solution or the emulsion within 3 minutes.

19. A method of making a solid composition, comprising:
forming a liquid mixture comprising a solvent, bortezomib, and boric acid; and
lyophilizing the liquid mixture,
where the mass ratio of the boric acid to the bortezomib in the liquid mixture is from 1:1 to 10:1, and where the solvent includes water and 1-20% by volume of a water-miscible organic solvent selected from the group consisting of ethanol, isopropanol, and tert-butanol.

20. A composition, formed by a method comprising:

forming a liquid mixture comprising a solvent, bortezomib, and boric acid, where the solvent includes water and 1-20% by volume of a water-miscible organic solvent selected from the group consisting of ethanol, isopropanol, and tert-butanol, where the mass ratio of boric acid to bortezomib in the liquid mixture is from 1:1 to 10:1; and lyophilizing the liquid mixture to form a solid composition.

* * * * *